United States Patent
Hasenberg et al.

(10) Patent No.: US 10,538,488 B2
(45) Date of Patent: Jan. 21, 2020

(54) SYNTHESIS OF METHYL ETHYL SULFIDE AND RELATED PRODUCTION SYSTEMS

(71) Applicant: Chevron Phillips Chemical Company LP, The Woodlands, TX (US)

(72) Inventors: Daniel M. Hasenberg, Kingwood, TX (US); Kenneth M. Lassen, Bartlesville, OK (US); Jason L. Kreider, Copan, OK (US); Henry Hwu, Houston, TX (US)

(73) Assignee: Chevron Phillips Chemical Company LP, The Woodlands, TX (US)

( * ) Notice: Subject to any disclaimer, the term of this patent is extended or adjusted under 35 U.S.C. 154(b) by 0 days.

(21) Appl. No.: 16/291,014

(22) Filed: Mar. 4, 2019

(65) Prior Publication Data
US 2019/0270702 A1 Sep. 5, 2019

Related U.S. Application Data

(60) Provisional application No. 62/753,965, filed on Nov. 1, 2018, provisional application No. 62/638,344, filed on Mar. 5, 2018.

(51) Int. Cl.
| | |
|---|---|
| *C07C 319/20* | (2006.01) |
| *C07C 319/28* | (2006.01) |
| *C07C 319/14* | (2006.01) |
| *C07C 319/08* | (2006.01) |
| *C07C 319/24* | (2006.01) |
| *C07C 321/14* | (2006.01) |
| *C07C 323/14* | (2006.01) |

(52) U.S. Cl.
CPC .......... *C07C 319/20* (2013.01); *C07C 319/08* (2013.01); *C07C 319/14* (2013.01); *C07C 319/24* (2013.01); *C07C 319/28* (2013.01); *C07C 321/14* (2013.01); *C07C 323/14* (2013.01)

(58) Field of Classification Search
None
See application file for complete search history.

(56) References Cited

U.S. PATENT DOCUMENTS

| | | |
|---|---|---|
| 4,005,129 A | 1/1977 | Zehner |
| 4,059,636 A | 11/1977 | Kubicek |
| 4,277,623 A | 7/1981 | Kubicek |
| 4,510,336 A | 4/1985 | Hearn |
| 4,537,994 A | 8/1985 | Roberts |
| 5,712,357 A | 1/1998 | Basset et al. |
| 2007/0135658 A1 | 6/2007 | Hasenberg et al. |
| 2019/0270703 A1 | 9/2019 | Hasenberg et al. |

OTHER PUBLICATIONS

McAllan et al., J. Amer. Chem. Soc., 1951, 73:3627-3632. (Year: 1951).*
International Search Report and the Written Opinion of the International Searching Authority in PCT/US2019/020533 dated May 10, 2019, 15 pages.
International Search Report and the Written Opinion of the International Searching Authority in PCT/US2019/020540 dated May 10, 2019, 16 pages.
McAllan et al., "The Preparation and Properties of Sulfur Compounds Related to Petroleum. 1. The Dialkyl Sulfides and Disulfides," Journal of the American Chemical Society 1951, vol. 73, No. 8, pp. 3627-3632.

* cited by examiner

*Primary Examiner* — Clinton A Brooks
*Assistant Examiner* — Kofi Adzamli
(74) *Attorney, Agent, or Firm* — Merchant & Gould P.C.

(57) ABSTRACT

The present invention discloses processes for producing methyl ethyl sulfide by contacting dimethyl sulfide and diethyl sulfide in the presence of a suitable catalyst. Methyl ethyl sulfide can be used as an odorant in natural gas. Integrated mercaptan and sulfide manufacturing systems and integrated methods for making mercaptans and sulfides also are disclosed.

11 Claims, 5 Drawing Sheets

SYNTHESIS OF METHYL ETHYL SULFIDE AND RELATED PRODUCTION SYSTEMS

REFERENCE TO RELATED APPLICATIONS

This application claims the benefit of U.S. Provisional Patent Application No. 62/638,344, filed on Mar. 5, 2018, and U.S. Provisional Application No. 62/753,965, filed on Nov. 1, 2018, the disclosures of which are incorporated herein by reference in their entirety.

FIELD OF THE INVENTION

The present disclosure relates to integrated mercaptan and sulfide manufacturing systems and integrated methods for making mercaptans and sulfides, and more particularly, relates to such systems and methods in which methyl ethyl sulfide is produced by reacting dimethyl sulfide and diethyl sulfide in the presence of a catalyst.

BACKGROUND OF THE INVENTION

Methyl ethyl sulfide can be prepared by reacting a suitable symmetrical sulfide with a suitable mercaptan, but this technique results in significant mercaptan byproducts. Methyl ethyl sulfide also can be prepared by reacting sodium methyl mercaptide and ethyl chloride, but significant waste products also are produced. Thus, the present invention is generally directed to a synthesis scheme to produce methyl ethyl sulfide in high yield and with minimal reaction byproducts.

SUMMARY OF THE INVENTION

This summary is provided to introduce a selection of concepts in a simplified form that are further described below in the detailed description. This summary is not intended to identify required or essential features of the claimed subject matter. Nor is this summary intended to be used to limit the scope of the claimed subject matter.

Integrated mercaptan and sulfide manufacturing systems are described herein. Such systems can comprise (i) a mercaptan production system capable of producing methyl mercaptan and dimethyl sulfide from methanol and $H_2S$ and capable of producing ethyl mercaptan and diethyl sulfide from ethanol and $H_2S$; (ii) a DMDS production system for consuming at least a portion of the methyl mercaptan from the mercaptan production system, wherein the DMDS production system is capable of producing dimethyl disulfide from the methyl mercaptan; (iii) an ETE production system for consuming at least a portion of the ethyl mercaptan from the mercaptan production system, wherein the ETE production system is capable of producing ethylthioethanol from the ethyl mercaptan; and (iv) a MES production system for consuming at least a portion of the dimethyl sulfide and the diethyl sulfide from the mercaptan production system, wherein the MES production system is capable of producing methyl ethyl sulfide from the dimethyl sulfide and the diethyl sulfide.

Integrated methods for producing mercaptans and sulfides also are provided herein. Such methods can comprise (a) reacting methanol and $H_2S$ to form methyl mercaptan and dimethyl sulfide, (b) reacting ethanol and $H_2S$ to form ethyl mercaptan and diethyl sulfide, (c) reacting at least a portion of the methyl mercaptan with hydrogen peroxide and sodium hydroxide to form dimethyl disulfide, (d) reacting at least a portion of the ethyl mercaptan with ethylene oxide to form ethylthioethanol, and (e) reacting at least a portion of the dimethyl sulfide and the diethyl sulfide to form methyl ethyl sulfide.

Consistent with aspects of this invention, a process for producing methyl ethyl sulfide also is disclosed herein, and this process can comprise contacting dimethyl sulfide, diethyl sulfide, and a catalyst to form a reaction mixture containing the methyl ethyl sulfide.

Both the foregoing summary and the following detailed description provide examples and are explanatory only. Accordingly, the foregoing summary and the following detailed description should not be considered to be restrictive. Further, features or variations may be provided in addition to those set forth herein. For example, certain aspects may be directed to various feature combinations and sub-combinations described in the detailed description.

BRIEF DESCRIPTION OF THE FIGURES

The following figures form part of the present specification and are included to further demonstrate certain aspects of the present invention. The invention may be better understood by reference to one or more of these figures in combination with the detailed description and examples.

DEFINITIONS

To define more clearly the terms used herein, the following definitions are provided. Unless otherwise indicated, the following definitions are applicable to this disclosure. If a term is used in this disclosure but is not specifically defined herein, the definition from the IUPAC Compendium of Chemical Terminology, $2^{nd}$ Ed (1997), can be applied, as long as that definition does not conflict with any other disclosure or definition applied herein, or render indefinite or non-enabled any claim to which that definition is applied. To the extent that any definition or usage provided by any document incorporated herein by reference conflicts with the definition or usage provided herein, the definition or usage provided herein controls.

Herein, features of the subject matter are described such that, within particular aspects, a combination of different features can be envisioned. For each and every aspect and each and every feature disclosed herein, all combinations that do not detrimentally affect the systems, compositions, processes, or methods described herein are contemplated with or without explicit description of the particular combination. Additionally, unless explicitly recited otherwise, any aspect or feature disclosed herein can be combined to describe inventive systems, compositions, processes, or methods consistent with the present disclosure.

Generally, groups of elements are indicated using the numbering scheme indicated in the version of the periodic table of elements published in *Chemical and Engineering News*, 63(5), 27, 1985. In some instances, a group of elements can be indicated using a common name assigned to the group; for example, alkali metals for Group 1 elements, alkaline earth metals for Group 2 elements, transition metals for Group 3-12 elements, and halogens or halides for Group 17 elements.

The term "hydrocarbon" whenever used in this specification and claims refers to a compound containing only carbon and hydrogen, whether saturated or unsaturated. Other identifiers can be utilized to indicate the presence of particular groups in the hydrocarbon (e.g., halogenated hydrocarbon indicates the presence of one or more halogen atoms replacing an equivalent number of hydrogen atoms in the hydrocarbon). The term "hydrocarbyl group" is used herein in accordance with the definition specified by IUPAC: a univalent group formed by removing a hydrogen atom from a hydrocarbon (that is, a group containing only carbon and hydrogen). Non-limiting examples of hydrocarbyl groups include alkyl, alkenyl, aryl, and aralkyl groups, amongst other groups.

For any particular compound or group disclosed herein, any name or structure (general or specific) presented is intended to encompass all conformational isomers, regioisomers, stereoisomers, and mixtures thereof that can arise from a particular set of substituents, unless otherwise specified. The name or structure (general or specific) also encompasses all enantiomers, diastereomers, and other optical isomers (if there are any) whether in enantiomeric or racemic forms, as well as mixtures of stereoisomers, as would be recognized by a skilled artisan, unless otherwise specified. For instance, a general reference to pentane includes n-pentane, 2-methyl-butane, and 2,2-dimethylpropane; and a general reference to a butyl group includes a n-butyl group, a sec-butyl group, an iso-butyl group, and a t-butyl group.

Unless otherwise specified, the term "substituted" when used to describe a group, for example, when referring to a substituted analog of a particular group, is intended to describe any non-hydrogen moiety that formally replaces a hydrogen in that group, and is intended to be non-limiting. Also, unless otherwise specified, a group or groups can also be referred to herein as "unsubstituted" or by equivalent terms such as "non-substituted," which refers to the original group in which a non-hydrogen moiety does not replace a hydrogen within that group. Moreover, unless otherwise specified, "substituted" is intended to be non-limiting and include inorganic substituents or organic substituents as understood by one of ordinary skill in the art.

The terms "contact product," "contacting," and the like, are used herein to describe methods and compositions wherein the components are contacted together in any order, in any manner, and for any length of time, unless otherwise specified. For example, the components can be contacted by blending or mixing. Further, unless otherwise specified, the contacting of any component can occur in the presence or absence of any other component of the methods and compositions described herein. Combining additional materials or components can be done by any suitable method. Further, the term "contact product" includes mixtures, blends, solutions, slurries, reaction products, and the like, or combinations thereof. Although "contact product" can, and often does, include reaction products, it is not required for the respective components to react with one another. Consequently, depending upon the circumstances, a "contact product" can be a mixture, a reaction mixture, or a reaction product. Likewise, "contacting" two or more components can result in a reaction product or a reaction mixture.

In this disclosure, while systems, compositions, and processes are described in terms of "comprising" various components or steps, the systems, compositions, and processes also can "consist essentially of" or "consist of" the various components or steps, unless stated otherwise.

The terms "a," "an," and "the" are intended to include plural alternatives, e.g., at least one. For instance, the disclosure of "a catalyst" is meant to encompass one catalyst, or mixtures or combinations of more than one catalyst, unless otherwise specified.

Several types of ranges are disclosed in the present invention. When a range of any type is disclosed or claimed, the intent is to disclose or claim individually each possible number that such a range could reasonably encompass, including end points of the range as well as any sub-ranges and combinations of sub-ranges encompassed therein. For example, the molar ratio of dimethyl sulfide to diethyl sulfide can be in certain ranges in various aspects of this invention. By a disclosure that the molar ratio of dimethyl sulfide to diethyl sulfide can be in a range from about 1.5:1 to about 10:1, the intent is to recite that the molar ratio can be any ratio in the range and, for example, can be equal to about 1.5:1, about 2:1, about 3:1, about 4:1, about 5:1, about 6:1, about 7:1, about 8:1, about 9:1, or about 10:1. Additionally, the molar ratio can be within any range from about 1.5:1 to about 10:1 (for example, from about 2:1 to about 6:1), and this also includes any combination of ranges between about 1.5:1 and about 10:1 (for example, the ratio can be in a range from about 1.5:1 to about 5:1, or from about 7:1 to about 9:1). Further, in all instances, where "about" a particular value is disclosed, then that value itself is disclosed. Thus, the disclosure of a molar ratio from about 1.5:1 to about 10:1 also discloses a molar ratio from 1.5:1 to 10:1 (for example, from 2:1 to 6:1), and this also includes any combination of ranges between 1.5:1 and 10:1 (for example, the ratio can be in a range from 1.5:1 to 5:1, or from 7:1 to 9:1). Likewise, all other ranges disclosed herein should be interpreted in a manner similar to this example.

The term "about" means that amounts, sizes, formulations, parameters, and other quantities and characteristics are not and need not be exact, but may be approximate including being larger or smaller, as desired, reflecting tolerances, conversion factors, rounding off, measurement errors, and the like, and other factors known to those of skill in the art. In general, an amount, size, formulation, parameter or other quantity or characteristic is "about" or "approximate" whether or not expressly stated to be such. The term "about" also encompasses amounts that differ due to different equilibrium conditions for a composition resulting from a particular initial mixture. Whether or not modified by the term "about," the claims include equivalents to the quantities. The term "about" can mean within 10% of the reported numerical value, and often within 5% of the reported numerical value.

All disclosed product yields are based on the limiting reactant in the respective reaction, unless explicitly stated otherwise. For example, the limiting reactant in a process for synthesizing methyl ethyl sulfide can be diethyl sulfide, therefore, the conversions and yields are based on the initial quantity of the diethyl sulfide.

Although any methods, devices, and materials similar or equivalent to those described herein can be used in the practice or testing of the invention, the typical methods, devices, and materials are herein described.

All publications and patents mentioned herein are incorporated herein by reference for the purpose of describing and disclosing, for example, the constructs and methodologies that are described in the publications, which might be used in connection with the presently described invention.

DETAILED DESCRIPTION OF THE INVENTION

Disclosed herein are processes for producing methyl ethyl sulfide by contacting dimethyl sulfide and diethyl sulfide with a catalyst in fixed bed reactor. These processes can be conducted with an excess of dimethyl sulfide, such that diethyl sulfide is the limiting reactant. Advantageously, the disclosed processes have excellent conversion of the diethyl sulfide and yield to methyl ethyl sulfide.

The methyl ethyl sulfide produced in accordance with this disclosure can be used as an odorant in natural gas. Beneficially, methyl ethyl sulfide has a boiling point in a desirable temperature range and a low freezing point, and is less prone to odor fade as compared to mercaptan-based odorants.

Also disclosed are integrated mercaptan and sulfide manufacturing systems and integrated methods for making mercaptans and sulfides, and these systems and methods incorporate the production of methyl ethyl sulfide from dimethyl sulfide and diethyl sulfide.
Synthesizing Methyl Ethyl Sulfide Aspects of this invention are directed to a process for producing methyl ethyl sulfide. This process can comprise contacting (a) dimethyl sulfide, (b) diethyl sulfide, and (c) a catalyst, to form a reaction mixture comprising the methyl ethyl sulfide. Generally, the features of this process for producing methyl ethyl sulfide (e.g., the catalyst and the conditions under which the methyl ethyl sulfide is formed, among others) are independently described herein and these features can be combined in any combination to further describe the disclosed process to produce methyl ethyl sulfide. Moreover, additional process steps can be performed before, during, and/or after the contacting/reacting step of this process, and can be utilized without limitation and in any combination to further describe the methyl ethyl sulfide synthesis process, unless stated otherwise.

Generally, the appropriate procedure for the contacting (or reacting) step in the process for producing methyl ethyl sulfide is not particularly limited. For instance, the step of contacting (or reacting) dimethyl sulfide, diethyl sulfide, and the catalyst can comprise contacting the dimethyl sulfide, diethyl sulfide, and catalyst in any order that produces an acceptable yield of methyl ethyl sulfide. Typically, the dimethyl sulfide and the diethyl sulfide are combined first, followed by contacting the mixture of dimethyl sulfide and diethyl sulfide with the catalyst.

The processes to produce methyl ethyl sulfide can be conducted at any suitable temperature and for any suitable period of time. Representative and non-limiting ranges for the temperature of the contacting step (or for the formation of the methyl ethyl sulfide) can include from about 200° C. to about 500° C., from about 250° C. to about 500° C., from about 200° C. to about 450° C., from about 250° C. to about 450° C., from about 125° C. to about 400° C., from about 200° C. to about 400° C., from about 200° C. to about 350° C., from about 250° C. to about 400° C., or from about 250° C. to about 350° C. These temperature ranges also are meant to encompass circumstances where the contacting step (or the formation of the methyl ethyl sulfide) is performed at a series of different temperatures, instead of at a single fixed temperature, falling within the respective temperature ranges, wherein at least one temperature is within the recited ranges.

Similarly, the time period for contacting the dimethyl sulfide, the diethyl sulfide, and the catalyst (or for the formation of the methyl ethyl sulfide) is not particularly limited, and can be conducted for any suitable period of time. In some aspects, the time period can be least about 1 minute, at least about 5 minutes, at least about 10 minutes, at least about 30 minutes, at least about 1 hour, at least about 2 hours, at least about 5 hours, or at least about 10 hours. In other aspects, the time period can be from about 30 seconds to about 48 hours, from about 1 minute to about 24 hours, from about 5 minutes to about 8 hours, from about 30 minutes to about 8 hours, or from about 1 hour to about 6 hours.

Often, the process for forming the methyl ethyl sulfide can be a flow process and/or a continuous process. In such circumstances, the limiting reactant-catalyst contact time (or reaction time) can be expressed in terms of weight hourly space velocity (WHSV)—the ratio of the weight of the limiting reactant which comes in contact with a given weight of catalyst per unit time (units of g/g/hr).

While not limited thereto, the WHSV employed for the process of producing methyl ethyl sulfide can have a minimum value of 0.01, 0.02, 0.05, 0.1, 0.25, or 0.5; or alternatively, a maximum value of 5, 4, 3, 2.5, 2, or 1. Generally, the WHSV can be in a range from any minimum WHSV disclosed herein to any maximum WHSV disclosed herein. In a non-limiting aspect, the WHSV can be in a range from about 0.01 to about 5; alternatively, from about 0.01 to about 3; alternatively, from about 0.01 to about 1; alternatively, from about 0.02 to about 4; alternatively, from about 0.02 to about 3; alternatively, from about 0.05 to about 2; alternatively, from about 0.05 to about 1; alternatively, from about 0.1 to about 4; alternatively, from about 0.25 to about 3; alternatively, from about 0.25 to about 2; alternatively, from about 0.5 to about 4; alternatively, from about 0.5 to about 2; or alternatively, from about 0.5 to about 1. Other WHSV ranges are readily apparent from this disclosure. Any suitable reactor or vessel can be used to form the methyl ethyl sulfide, non-limiting examples of which can include a flow reactor, a continuous reactor, a packed tube, and a stirred tank reactor, including more than one reactor in series or in parallel, and including any combination of reactor types and arrangements.

In one aspect, the process for producing methyl ethyl sulfide can comprise contacting the dimethyl sulfide and the diethyl sulfide in the vapor phase with the catalyst (e.g., the solid catalyst). Additionally or alternatively, the process for producing methyl ethyl sulfide can comprise contacting the dimethyl sulfide and the diethyl sulfide with a fixed bed of the catalyst.

While not being limited thereto, the contacting step and/or the formation of the methyl ethyl sulfide can be conducted at a reaction pressure in a range from about 50 to about 850 psig (344 to 5860 kPag). Other representative and non-limiting ranges for the reaction pressure can include from about 50 to about 500 psig (344 to 3447 kPag), from about 100 to about 400 psig (689 to 2758 kPag), from about 150 to about 400 psig (1034 to 2758 kPag), from about 200 to about 450 psig (1379 to 3103 kPag), or from about 200 to about 350 psig (1379 to 2413 kPag).

The molar ratio of dimethyl sulfide to diethyl sulfide (DMS:DES) is not particularly limited, and generally can fall within a range from about 10:1 to about 1:10. Typical ranges for the molar ratio of the dimethyl sulfide to diethyl sulfide (DMS:DES) can include, but are not limited to, from about 5:1 to about 1:5, from about 4:1 to about 1:4, from about 3:1 to about 1:3, from about 2:1 to about 1:2, or from about 1.5:1 to about 1:1.5.

Certain ratios of components during the contacting step can prove advantageous with respect to the yield and purity of the resultant methyl ethyl sulfide. In one aspect, the molar ratio of DMS:DES can be greater than about 1:1, greater than about 1.2:1, greater than about 1.5:1, greater than about 2:1, greater than about 3:1, or greater than about 5:1. In such circumstances, the diethyl sulfide can be the limiting reactant in the process for producing the methyl ethyl sulfide. Typical non-limiting ranges for the molar ratio of DMS: DES, therefore, can include from about 1.2:1 to about 15:1, from about 1.5:1 to about 10:1, from about 1.5:1 to about 6:1, from about 2:1 to about 10:1, from about 4:1 to about 20:1, or from about 2:1 to about 6:1. It should be noted that an excess of the dimethyl sulfide can promote greater yield of the methyl ethyl sulfide compound.

Optionally, the process for producing methyl ethyl sulfide can further include an additional sulfur-containing reactant. That is, the process can comprise contacting the dimethyl sulfide, the diethyl sulfide, the catalyst, and a sulfur-containing compound. Illustrative and non-limiting examples of the sulfur-containing compound include $H_2S$, $CS_2$, di-tert-butyl polysulfide, and the like, as well as any combination thereof. While not wishing to be bound by the following theory, it is believed that small amounts of such sulfur-containing materials can improve the yield of the methyl ethyl sulfide. Any suitable amount of the sulfur-containing compound can be used, from an amount greater than zero and typically less than or equal to about 5 mol %. More often, the addition amount can be less than or equal to about 3 mol %, or less than or equal to about 1 mol %. These mole percentages are based on the moles of the limiting reactant (e.g., diethyl sulfide). The di-tert-butyl polysulfide material is low in odor and non-volatile, and therefore can be conveniently used in the disclosed processes.

The processes described herein result in an unexpectedly high conversion of the limiting reactant and/or yield to the methyl ethyl sulfide. In one aspect, the minimum conversion (or yield) can be at least about 50%, at least about 60%, at least about 70%, at least about 80%, at least about 90%, or at least about 95%. Additionally, the maximum conversion (or yield) can be about 97%, about 98%, about 99%, or about 99.5%, and can approach 100% conversion of the limiting reactant (or yield of the methyl ethyl sulfide). Generally, the conversion (or yield) can be in a range from any minimum conversion (or yield) disclosed herein to any maximum conversion (or yield) disclosed herein. Non-limiting ranges of conversion (or yield) can include from about 50% to about 99.5%, from about 80% to about 99%, from about 90% to about 98%, or from about 95% to 100%. For conversion, the percentages are the amount of the limiting reactant converted based on the initial amount of the limiting reactant. The yield values are mole percentages and are based on the moles of methyl ethyl sulfide produced to moles of the limiting reactant. In some aspects, these conversions (or yields) can be achieved in a batch process, while in other aspects, these conversions (or yields) can be achieved in a flow or continuous process, such as, for example, a single pass or multiple passes through a reactor (e.g., a fixed bed reactor).

Also unexpectedly, continuous flow processes for producing the methyl ethyl sulfide in accordance with this invention have unexpectedly high single pass conversions of the limiting reactant (or single pass yields to the methyl ethyl sulfide). In one aspect, the minimum single pass conversion (or yield) can be at least about 40%, at least about 50%, at least about 60%, at least about 70%, at least about 80%, or at least about 85%. Additionally, the maximum single pass conversion (or yield) can be about 90%, about 95%, about 98%, or about 99%, and can approach 100% conversion of the limiting reactant (or yield of the methyl ethyl sulfide), depending upon the reaction conditions. Generally, the single pass conversion (or yield) can be in a range from any minimum single pass conversion (or yield) disclosed herein to any maximum single pass conversion (or yield) disclosed herein. Non-limiting ranges of single pass conversion (or yield) can include from about 40% to about 90%, from about 50% to about 90%, from about 60% to about 95%, from about 70% to about 98%, or from about 80% to 100%.

The processes to produce methyl ethyl sulfide disclosed herein typically result in a crude reaction mixture containing the methyl ethyl sulfide, residual reactants, and relatively minor amounts of byproducts (e.g., mercaptans, sulfide heavies). Beneficially, and unexpectedly, the amount of mercaptan products (such as methyl mercaptan and/or ethyl mercaptan) in the reaction mixture is very low. For instance, in one aspect, the reaction mixture can contain less than or equal to about 5 wt. % mercaptan products (or less than or equal to about 5 wt. % methyl mercaptan, or less than or equal to about 5 wt. % ethyl mercaptan), while in another aspect, the reaction mixture can contain less than or equal to about 3 wt. % mercaptan products (or less than or equal to about 3 wt. % methyl mercaptan, or less than or equal to about 3 wt. % ethyl mercaptan), and in yet another aspect, the reaction mixture can contain less than or equal to about 2 wt. % (or 1 wt. %) mercaptan products (or less than or equal to about 2 wt. % (or 1 wt. %) methyl mercaptan, or less than or equal to about 2 wt. % (or 1 wt. %) ethyl mercaptan).

In many instances, it can be desirable to isolate the methyl ethyl sulfide from the reaction mixture for sale or for use in further industrial processes. Accordingly, in certain aspects, the process for producing methyl ethyl sulfide can further comprise a step of isolating the methyl ethyl sulfide from the reaction mixture to form a product stream containing the methyl ethyl sulfide. Isolation of the methyl ethyl sulfide can employ any suitable technique for separating the methyl ethyl sulfide from other components of the reaction mixture, in order to form a product stream containing the methyl ethyl sulfide. Such techniques can include, but are not limited to, extraction, filtration, evaporation, or distillation, as well as combinations of two or more of these techniques. In particular aspects of this invention, the isolating step utilizes distillation at any suitable pressure (one or more than one distillation column can be used). Advantageously, the low levels of mercaptans in the reaction mixture make isolating the methyl ethyl sulfide via distillation a relatively straightforward process.

Additionally, other components of the reaction mixture (e.g., dimethyl sulfide and diethyl sulfide) can be recovered and recycled to the reactor. In such instances, the limiting reactant can be recycled to extinction, such that all or substantially all (>99 mol %) of the limiting reactant (e.g., diethyl sulfide) is converted to the methyl ethyl sulfide (or to a byproduct).

After isolating, and unexpectedly, the processes to produce methyl ethyl sulfide disclosed herein can result in a high yield of the methyl ethyl sulfide in the product stream. Generally, the methyl ethyl sulfide can be produced in a yield of at least about 40 mol %, and more often, at least about 60 mol %, at least about 70 mol %, at least about 80 mol %, at least about 90 mol %, or at least about 95 mol %, and often as high as 98-100 mol %, in the product stream.

This yield is based on the moles of the limiting reactant, which is often the diethyl sulfide. Generally, purification steps to isolate a desired product from a crude reaction mixture reduce the overall yield of the desired product. However, consistent with this invention, the isolated methyl ethyl sulfide can be recovered in a yield similar to that of the crude methyl ethyl sulfide.

After the isolating step, the methyl ethyl sulfide can have a purity of at least about 80 wt. %, at least about 85 wt. %, at least about 90 wt. %, at least about 95 wt. %, at least about 97 wt. %, or at least about 99 wt. %, in the product stream. The purity is based on the weight of the methyl ethyl sulfide in the product stream to the total weight of the product stream.

The catalyst compositions used in the processes disclosed herein are not particularly limited, so long as they are able to promote a reaction between dimethyl sulfide and diethyl sulfide to produce methyl ethyl sulfide, as described herein. In one aspect, the catalyst can comprise any suitable solid hydrotreating catalyst. In another aspect, the catalyst can comprise a CoMo catalyst, a NiMo catalyst, and the like, as well as any combination thereof. In yet another aspect, the catalyst (e.g., the CoMo and/or NiMo catalyst) can be pre-sulfided to increase the conversion of the limiting reactant and the yield of the methyl ethyl sulfide.

As would be recognized by one of skill in the art, the catalyst can be supported on any suitable solid oxide or like material. Thus, the catalyst can further comprise a support or solid oxide, illustrative examples of which can include silica, alumina, silica-alumina, aluminum phosphate, zinc aluminate, zirconia, thoria, and the like. Combinations of more than one support material can be used for the catalyst.

Consistent with another aspect of this invention, the catalyst does not contain a transition metal. For instance, the catalyst can comprise (or consist essentially of, or consist of) γ-alumina in one aspect of this invention. In another aspect, the catalyst can comprise a molecular sieve or a zeolite (a crystalline aluminosilicate), such as a Y-zeolite (zeolite Y) or a X-zeolite (zeolite X). Zeolites can exhibit a network of $SiO_4$ and $AlO_4$ tetrahedra in which aluminum and silicon atoms are crosslinked in a three-dimensional framework by sharing oxygen atoms. In the framework, the ratio of oxygen atoms to the total of aluminum and silicon atoms can be equal to 2. The framework exhibits a negative electrovalence that typically can be balanced by the inclusion of cations within the crystal, such as metals, alkali metals, alkaline earth metals, hydrogen, or combinations thereof.

The Y-zeolite (zeolite Y) and X-zeolite (zeolite X) can have an average pore diameter in a range of from about 7 Å to about 12 Å. The Si:Al ratio for a X-zeolite is less than that for a Y-zeolite. Often, the zeolite can be bound with a support matrix (or binder), non-limiting examples of which can include silica, alumina, magnesia, boria, titania, zirconia, various clays, and the like, including mixed oxides thereof, as well as mixtures thereof.

In some aspects, the catalyst can comprise supported CoMo and an alkali or alkaline earth metal hydroxide, such as described in U.S. Pat. No. 4,277,623, incorporated herein by reference in its entirety. For instance, the catalyst can contain 3-4 wt. % cobalt oxide and 15-16 wt. % molybdenum oxide supported on alumina, although the respective amounts of Co and Mo are not limited thereto. Illustrative examples of suitable hydroxides can include, but are not limited to, lithium hydroxide, sodium hydroxide, potassium hydroxide, rubidium hydroxide, cesium hydroxide, magnesium hydroxide, calcium hydroxide, barium hydroxide, and the like, as well as combinations thereof. The hydroxide component can be in any form, but beneficially for the processes disclosed herein, can be in pellet form for use in a fixed or packed bed reactor configuration. The relative amounts of the supported CoMo component and the hydroxide component are not particularly limited, although an excess of the hydroxide component, on a weight basis, often can be used.

In some aspects, the catalyst can comprise a metal salt compound, typically palladium (II), rhodium (III), platinum (II), and/or copper (I) or (II) salt compounds, as described in U.S. Pat. No. 4,005,129, incorporated herein by reference in its entirety. The catalyst also can include an aliphatic, cycloaliphatic, aromatic, or heterocyclic amine or ammonia, as well as copper (II) or iron (III) oxidant compounds—e.g., a copper (II) oxalate, sulfate, acetate, or trifluoroacetate oxidant salt compound. Representative metal salt compounds can include, but are not limited to, palladium (II) chloride, copper (II) chloride, rhodium (III) chloride, copper (II) iodide, palladium (II) sulfate, palladium (II) oxalate, palladium (II) acetate, palladium (II) iodide, rhodium (III) bromide, platinum (II) chloride, platinum (II) sulfate, and the like, as well as combinations thereof. Any or all of the catalyst components can be supported on any suitable support material or solid oxide.

Integrated Mercaptan and Sulfide Manufacturing Systems

An integrated mercaptan and sulfide manufacturing system consistent with aspects of the present invention can comprise (i) a mercaptan production system capable of producing (or configured to produce) methyl mercaptan and dimethyl sulfide from methanol and $H_2S$, and capable of producing (or configured to produce) ethyl mercaptan and diethyl sulfide from ethanol and $H_2S$, (ii) a DMDS production system for consuming at least a portion of the methyl mercaptan from the mercaptan production system, wherein the DMDS production system is capable of producing (or configured to produce) dimethyl disulfide from the methyl mercaptan, (iii) an ETE production system for consuming at least a portion of the ethyl mercaptan from the mercaptan production system, wherein the ETE production system is capable of producing (or configured to produce) ethylthioethanol from the ethyl mercaptan, and (iv) a MES production system for consuming at least a portion of the dimethyl sulfide and the diethyl sulfide from the mercaptan production system, wherein the MES production system is capable of producing (or configured to produce) methyl ethyl sulfide from the dimethyl sulfide and the diethyl sulfide.

The mercaptan production system is capable of producing (or configured to produce) methyl mercaptan and dimethyl sulfide from methanol and $H_2S$ and is further capable of producing (or configured to produce) ethyl mercaptan and diethyl sulfide from ethanol and $H_2S$. The relative amount of methyl mercaptan (or ethyl mercaptan) produced as compared to the amount of dimethyl sulfide (or diethyl sulfide) can vary depending upon the process conditions and the amount of excess $H_2S$ used in the respective reaction. While not being limited thereto, at least about 70 wt. %, 80 wt. %, 85 wt. %, or 90 wt. % of the reaction products are methyl mercaptan (or ethyl mercaptan), with the amount of dimethyl sulfide (or diethyl sulfide) typically less than 30 wt. %, 20 wt. %, 15 wt. %, or 10 wt. % of the reaction products.

In the mercaptan production system, isolated product streams of methyl mercaptan (or ethyl mercaptan) and dimethyl sulfide (or diethyl sulfide) can be produced using any suitable separations technique (e.g., distillation) or a combination of suitable techniques.

The DMDS production system can consume at least a portion of the methyl mercaptan from the mercaptan production system. While not being limited thereto, at least about 75 wt. % of the methyl mercaptan from the mercaptan production system generally is consumed in the DMDS production system. In some aspects, at least about 85 wt. %, at least about 95 wt. %, at least about 99 wt. %, or all or substantially all, of the methyl mercaptan from the mercaptan production system can be consumed in the DMDS production system.

In the DMDS production system, dimethyl disulfide can be produced from the methyl mercaptan and, for example, hydrogen peroxide and sodium hydroxide. Often, at least about 80%, at least about 90%, at least about 95%, or at least about 99%, of the methyl mercaptan can be converted in the DMDS production system, and the yield of the dimethyl disulfide can be at least about 80%, at least about 90%, at least about 95%, or at least about 99% (these are molar yields based on the moles of methyl mercaptan).

The ETE production system can consume at least a portion of the ethyl mercaptan from the mercaptan production system. While not being limited thereto, at least about 80 wt. % of the ethyl mercaptan from the mercaptan production system generally is consumed in the ETE production system. In some aspects, at least about 90 wt. %, at least about 95 wt. %, at least about 99 wt. %, or all or substantially all, of the ethyl mercaptan from the mercaptan production system can be consumed in the ETE production system.

In the ETE production system, ethylthioethanol can be produced from the ethyl mercaptan and, for example, ethylene oxide. Often, at least about 80%, at least about 90%, at least about 95%, or at least about 99% of the ethyl mercaptan can be converted in the ETE production system, and the yield of the ethylthioethanol can be at least about 80%, at least about 90%, at least about 95%, or at least about 99% (these are molar yields based on the moles of ethyl mercaptan).

The MES production system can consume at least a portion of the dimethyl sulfide and the diethyl sulfide (i.e., at least a portion of the dimethyl sulfide, or at least a portion of the diethyl sulfide, or at least a portion of both the dimethyl sulfide and the diethyl sulfide) from the mercaptan production system. For example, at least about 75 wt. % of the diethyl sulfide from the mercaptan production system can be consumed in the MES production system. In some aspects, at least about 85 wt. %, at least about 95 wt. %, at least about 99 wt. %, or all or substantially all of the diethyl sulfide from the mercaptan production system can be consumed in the MES production system.

In the MES production system, methyl ethyl sulfide can be produced from the dimethyl sulfide and the diethyl sulfide. In one aspect, the MES production system can comprise a reactor capable of reacting (or configured to react) the dimethyl sulfide and the diethyl sulfide in the presence of a catalyst to form a reaction mixture containing the methyl ethyl sulfide. In another aspect, the MES production system can comprise a fixed bed reactor capable of reacting (or configured to react) the dimethyl sulfide and the diethyl sulfide in the vapor phase with a fixed bed of a catalyst to form a reaction mixture containing the methyl ethyl sulfide. In these and other aspects, the reactor can be constructed of any suitable stainless steel, non-limiting examples of which can include grade 304, 316, 321, 347, 410S, 600, or 800 stainless steels, among others.

The reactor in the MES production system can be capable of operating (or configured to operate) at a temperature in a range from about 200° C. to about 500° C. and at a pressure in a range from about 50 to about 500 psig (344 to 3447 kPag). In a further aspect, the reactor in the MES production system can be capable of operating (or configured to operate) at a temperature in a range from about 250° C. to about 450° C. and at a pressure in a range from about 100 to about 450 psig (689 to 3102 kPag). The catalyst used in the MES manufacturing system, whether employed in a fixed bed reactor or not, can be any suitable supported or unsupported hydrotreating catalyst or any catalyst disclosed herein, such as a CoMo catalyst, a NiMo catalyst, or γ-alumina, and the like, as well as combinations thereof.

The reactor in the MES manufacturing system can be capable of reacting (or configured to react) the diethyl sulfide and an excess of the dimethyl sulfide in the presence of a catalyst to form a reaction mixture containing the methyl ethyl sulfide at any suitable percent conversion of the diethyl sulfide (and/or yield of the methyl ethyl sulfide). Often, at least about 70%, at least about 80%, at least about 90%, or at least about 95%, of the diethyl sulfide can be converted in the MES reactor, and the yield of the methyl ethyl sulfide can be at least about 70%, at least about 80%, at least about 90%, or at least about 95% (these are molar yields based on the moles of diethyl sulfide).

As disclosed herein, the process for producing methyl ethyl sulfide can be a continuous flow process. In such circumstances, the MES reactor can be capable of reacting (or configured to react) the diethyl sulfide and an excess of the dimethyl sulfide in the presence of a catalyst to form a reaction mixture containing the methyl ethyl sulfide at any suitable single pass percent conversion of the diethyl sulfide (or yield of the methyl ethyl sulfide). Often, at least about 60%, at least about 70%, at least about 75%, or at least about 80%, of the diethyl sulfide can be converted in a single pass, and the single pass yield of the methyl ethyl sulfide can be at least about 60%, at least about 70%, at least about 75%, or at least about 80% (these are molar yields based on the moles of diethyl sulfide).

In addition to the reactor, the MES production system can comprise a downstream separations system capable of isolating (or configured to isolate) the methyl ethyl sulfide from the reaction mixture to form a product stream containing the methyl ethyl sulfide. In some aspects of this invention, the downstream separations system can be further capable of isolating (or configured to isolate) unreacted dimethyl sulfide and diethyl sulfide from the reaction mixture, and recycling the unreacted dimethyl sulfide and diethyl sulfide to the reactor. While not being limited thereto, the downstream separations system can comprise one or more than one distillation column.

The MES production system and the downstream separations system can be capable of forming (or configured to form) the product stream at a purity of the methyl ethyl sulfide in the product stream of at least about 90 wt. %, at least about 95 wt. %, at least about 97 wt. %, or at least about 99 wt. %. These weight percentages are based on the amount of methyl ethyl sulfide in the product stream to the total weight of the product stream.

Further, the MES production system and the downstream separations system can be capable of forming (or configured to form) the product stream at a yield of the methyl ethyl sulfide in the product stream of at least about 70%, at least about 80%, at least about 90%, or at least about 95%. These are molar yields based on the moles of diethyl sulfide.

Figure 1:
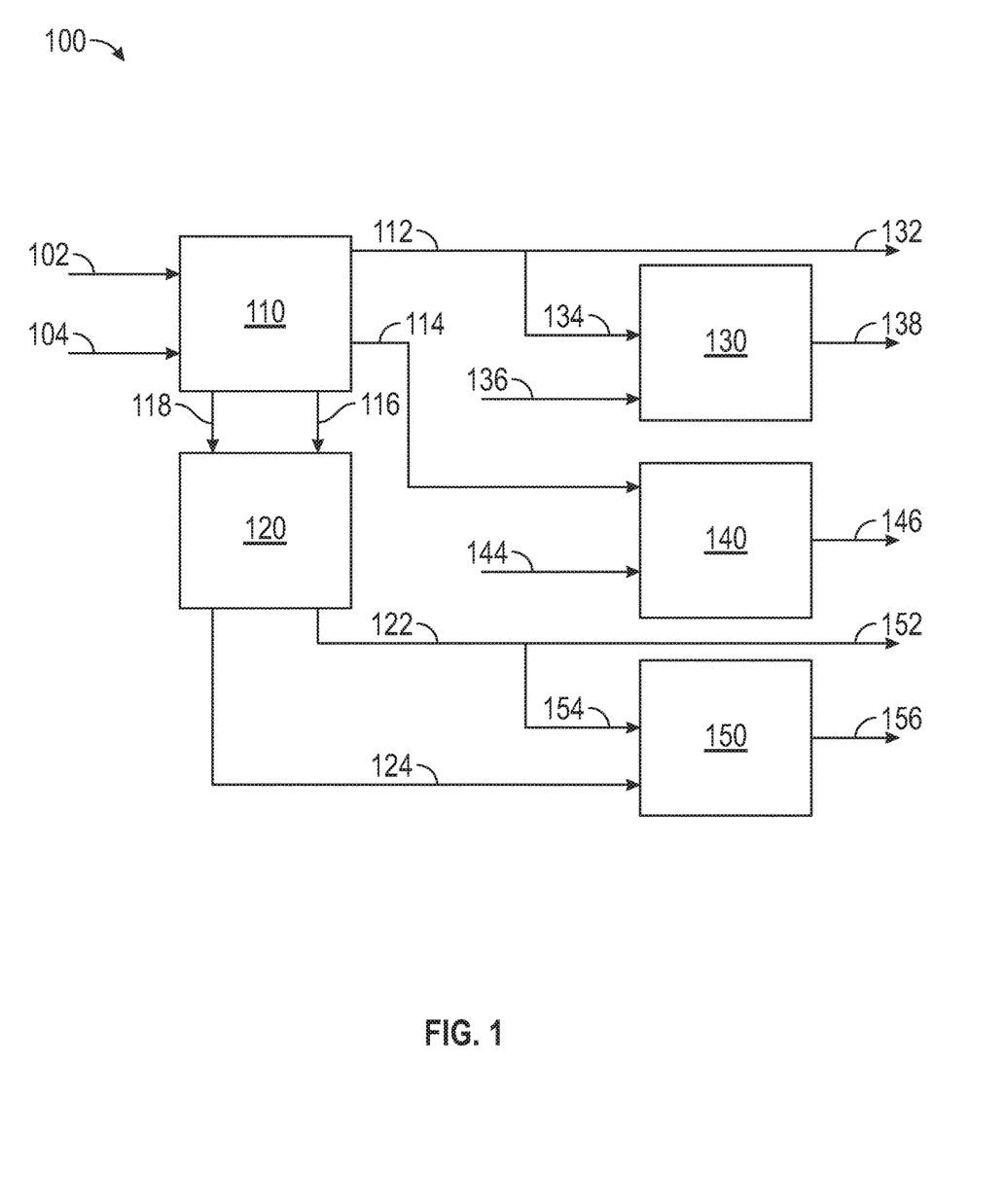
FIG. 1 illustrates an integrated mercaptan and sulfide manufacturing system consistent with an aspect of the present invention.

An integrated mercaptan and sulfide manufacturing system, as described herein, can contain a (i) a mercaptan production system, (ii) a DMDS production system, (iii) an ETE production system, and (iv) a MES production system. FIG. 1 illustrates a representative mercaptan and sulfide manufacturing system 100 consistent with the present invention. Mercaptan and sulfide manufacturing system 100 can include mercaptan production system 110, ETE (ethylthioethanol) production system 130, DMDS (dimethyl disulfide) production system 140, and MES (methyl ethyl sulfide) production system 150. In FIG. 1, mercaptan production system 110 includes alcohol reactant stream 102, which can feed methanol or ethanol (or both) to mercaptan production system 110, and $H_2S$ reactant stream 104, which can feed $H_2S$ to mercaptan production system 110. From these reactants, mercaptan production system 110 can produce methyl mercaptan product stream 114 and dimethyl sulfide product stream 116 (from the methanol and $H_2S$), as well as ethyl mercaptan product stream 112 and diethyl sulfide product stream 118 (from the ethanol and $H_2S$).

Ethyl mercaptan product stream 112 can be split such that a portion becomes ethyl mercaptan reactant stream 134, which can feed to ETE production system 130, as shown in FIG. 1. The remaining portion of ethyl mercaptan product stream 132 can be used for other purposes, such as for sale/distribution or for use in other industrial/chemical processes. ETE production system 130 also includes ethylene oxide reactant stream 136, and ETE production system 130 can produce ethylthioethanol product stream 138 from the ethyl mercaptan and ethylene oxide.

Although not shown, methyl mercaptan product stream 114 can be split in a similar manner to ethyl mercaptan product stream 112. In FIG. 1, methyl mercaptan feed stream 114 can feed directly to DMDS production system 140. DMDS production system 140 also includes a feed stream for other reactants 144 (e.g., hydrogen peroxide and sodium hydroxide), and DMDS production system 140 can produce dimethyl disulfide product stream 146 from the methyl mercaptan, hydrogen peroxide, and sodium hydroxide.

Storage tank system 120 can be used to store dimethyl sulfide from dimethyl sulfide product stream 116 and diethyl sulfide from diethyl sulfide product stream 118 for future use. Although not shown, storage tank system 120 also can store methyl mercaptan from methyl mercaptan product stream 114 and/or ethyl mercaptan from ethyl mercaptan product stream 112 for future use, if desired.

Dimethyl sulfide feed stream 122 exiting tank system 120 can be split such that a portion becomes dimethyl sulfide reactant stream 154, which can feed to MES production system 150, as shown in FIG. 1. The remaining portion of dimethyl sulfide feed stream 152 can be used for other purposes, such as for sale/distribution or for use in other industrial/chemical processes. Although not shown, diethyl sulfide reactant stream 124 can be split in a similar manner to dimethyl sulfide feed stream 122. In FIG. 1, diethyl sulfide reactant stream 124 can feed directly from tank system 120 to MES production system 150. MES production system 150 can produce methyl ethyl sulfide product stream 156 from the dimethyl sulfide and the diethyl sulfide.

Integrated Mercaptan and Sulfide Production Processes

Aspects of this invention also are directed to integrated methods for producing mercaptans and sulfides. Such processes can comprise, consist essentially of, or consist of (a) reacting methanol and $H_2S$ to form methyl mercaptan and dimethyl sulfide, (b) reacting ethanol and $H_2S$ to form ethyl mercaptan and diethyl sulfide, (c) reacting at least a portion of the methyl mercaptan with hydrogen peroxide and sodium hydroxide to form dimethyl disulfide, (d) reacting at least a portion of the ethyl mercaptan with ethylene oxide to form ethylthioethanol, and (e) reacting at least a portion of the dimethyl sulfide and the diethyl sulfide to form methyl ethyl sulfide. Generally, the features of this integrated method are independently described herein and these features can be combined in any combination to further describe the disclosed integrated method. Moreover, other process steps can be conducted before, during, and/or after any of steps (a)-(e), unless stated otherwise.

Generally, steps (a)-(e) can be conducted at any suitable reaction conditions (e.g., temperature, pressure, reactant ratio, etc.), as would be recognized by those skilled in the art.

In step (a), methanol and $H_2S$ can be reacted to form methyl mercaptan and dimethyl sulfide, and at least a portion of the methyl mercaptan can be reacted with hydrogen peroxide and sodium hydroxide in step (c) to form dimethyl disulfide. While not limited thereto, at least about 75 wt. %, at least about 85 wt. %, at least about 95 wt. %, or at least about 99 wt. %, of the methyl mercaptan produced in step (a) can be consumed in step (c). Additionally, the conversion of methyl mercaptan (or molar yield to the dimethyl disulfide) in step (c) can be at least about 80%, at least about 90%, at least about 95%, or at least about 99%.

In step (b), ethanol and $H_2S$ can be reacted to form ethyl mercaptan and diethyl sulfide, and at least a portion of the ethyl mercaptan can be reacted with ethylene oxide in step (d) to form ethylthioethanol. Any suitable amount of the ethyl mercaptan produced in step (b) can be consumed in step (d), ranging from less than 10 wt. % to over 90 wt. %. Additionally, the conversion of ethyl mercaptan (or molar yield to the ethylthioethanol) in step (d) can be at least about 80%, at least about 90%, at least about 95%, or at least about 99%.

Methanol and $H_2S$ can be reacted to form methyl mercaptan and dimethyl sulfide in step (a), and ethanol and $H_2S$ can be reacted to form ethyl mercaptan and diethyl sulfide in step (b). In step (e), at least a portion of the dimethyl sulfide and the diethyl sulfide can be reacted to form methyl ethyl sulfide. While not limited thereto, at least about 75 wt. %, at least about 85 wt. %, at least about 95 wt. %, or at least about 99 wt. %, of the diethyl sulfide produced in step (b) can be consumed in step (e). Any suitable amount of the dimethyl sulfide produced in step (a) can be consumed in step (e), ranging from less than 10 wt. % to over 90 wt. %.

Further, any features of the process for producing methyl ethyl sulfide (by contacting dimethyl sulfide, diethyl sulfide, and a catalyst to form a reaction mixture comprising the methyl ethyl sulfide) disclosed herein can be applied to step (e). For instance, dimethyl sulfide and diethyl sulfide can be reacted in the presence of a supported or unsupported catalyst (e.g., γ-alumina, a CoMo catalyst, or a NiMo catalyst), and the percent conversion of the diethyl sulfide (or the molar yield to the methyl ethyl sulfide) in step (e) can be at least about 70%, at least about 80%, at least about 90%, or at least about 95%. Moreover, the methyl ethyl sulfide can be isolated from the reaction mixture using any suitable technique (e.g., extraction, filtration, evaporation, distillation, or any combination thereof), to form a product stream containing the methyl ethyl sulfide. This product stream can contain, for instance, at least about 90 wt. %, at least about 95 wt. %, at least about 97 wt. %, or at least about 99 wt. %, of the methyl ethyl sulfide, based on the total weight of the product stream. Additionally or alternatively, unreacted dimethyl sulfide and unreacted diethyl sulfide can be isolated from the reaction mixture, and recycled or re-used as reactants in step (e).

EXAMPLES

The invention is further illustrated by the following examples, which are not to be construed in any way as imposing limitations to the scope of this invention. Various other aspects, modifications, and equivalents thereof, which after reading the description herein, can suggest themselves to one of ordinary skill in the art without departing from the spirit of the present invention or the scope of the appended claims.

Gas Chromatograph (GC) analyses were conducted on an Agilent 7890A GC System, using an HP-5 column (dimethylpolysiloxane, capillary 30 m×0.32 μm×0.25 μm nominal), with 35° C. temperature hold for 5 minutes followed by ramping at a rate of 5° C./min from 35° C. to 70° C., followed by ramping at 15° C./min to 260° C., then holding at 260° C. for 10 minutes. Standards for dimethyl sulfide (DMS), diethyl sulfide (DES), and methyl ethyl sulfide (MES) were used to identify the respective reactants and products. Product composition information is presented in area percentages (area %), unless otherwise specified.

Examples 1-16

Synthesis of Methyl Ethyl Sulfide

Figure 2:
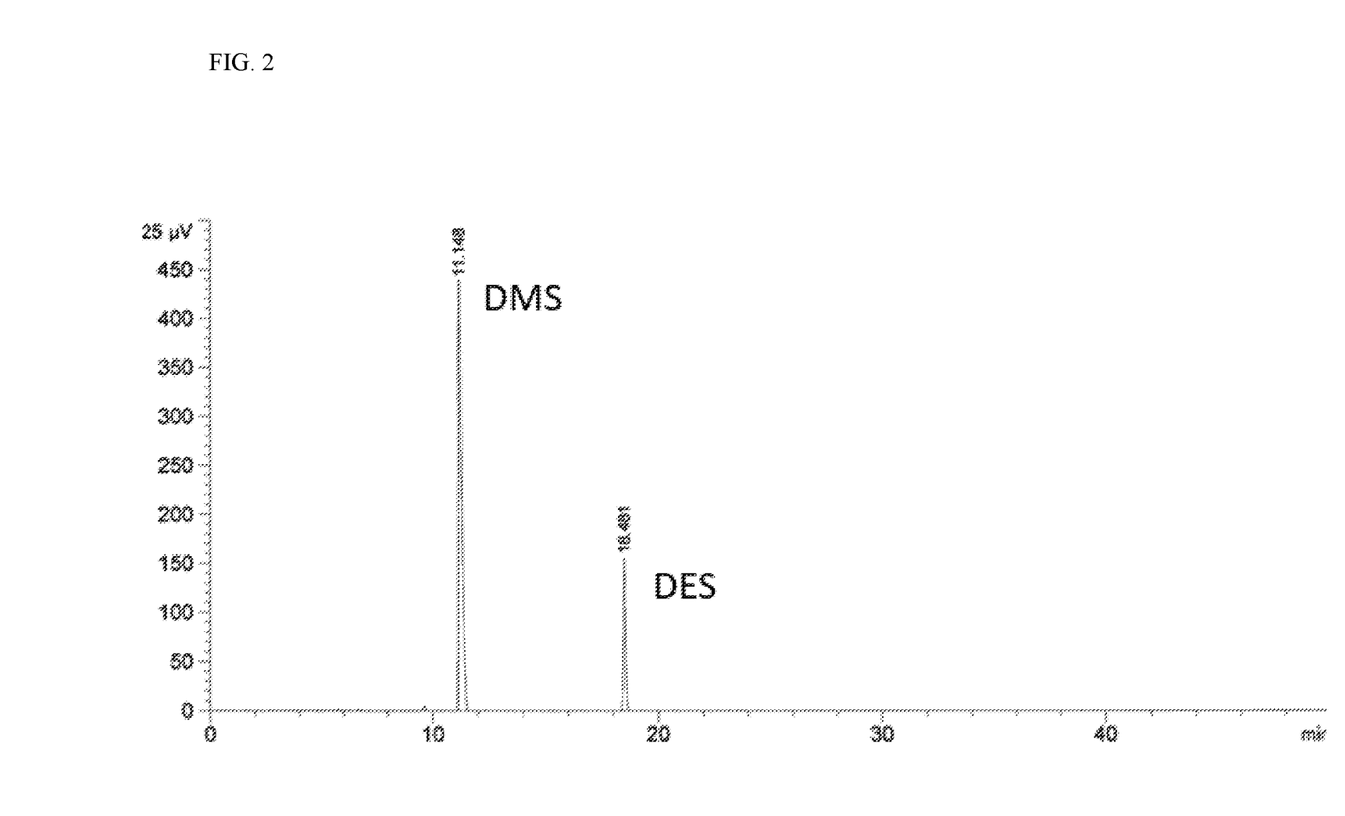
FIG. 2 presents a gas chromatograph plot of the blended feed of dimethyl sulfide and diethyl sulfide, which was used in Examples 1-15.

For Example 1, dimethyl sulfide (DMS) and diethyl sulfide (DES) were blended in a feed tank at an approximate weight ratio of 4:1 (DMS:DES), which was confirmed via GC. FIG. 2 is a GC plot of the blended feed containing DMS and DES. The respective amounts of DMS (eluting at 11 min; 79.3%) and DES (eluting at 18 min; 20.7%) via area percentages are listed in Table I.

The DMS and DES blend was fed into the top of a fixed bed reactor containing a mixed bed of (i) supported CoMo on alumina and (ii) γ-alumina at a total flow rate (DMS and DES) of 17 g/hr. The WHSV was 0.1 (weight of DES which comes in contact with the catalyst per unit time, in g/g/hr). The fixed bed reactor had three independent heating zones: the top zone of the reactor (5.71 g of γ-alumina and 6.85 g of supported CoMo), the middle zone of the reactor (8.41 g of γ-alumina and 3.31 g of supported CoMo), and the bottom zone of the reactor (10.7 g of γ-alumina). As shown in Table I, the reaction temperature was approximately 270-300° C., and the reaction pressure was 300 psig (2068 kPag). Unexpectedly, 90% of the DES was converted, primarily to methyl ethyl sulfide (MES).

Figure 3:
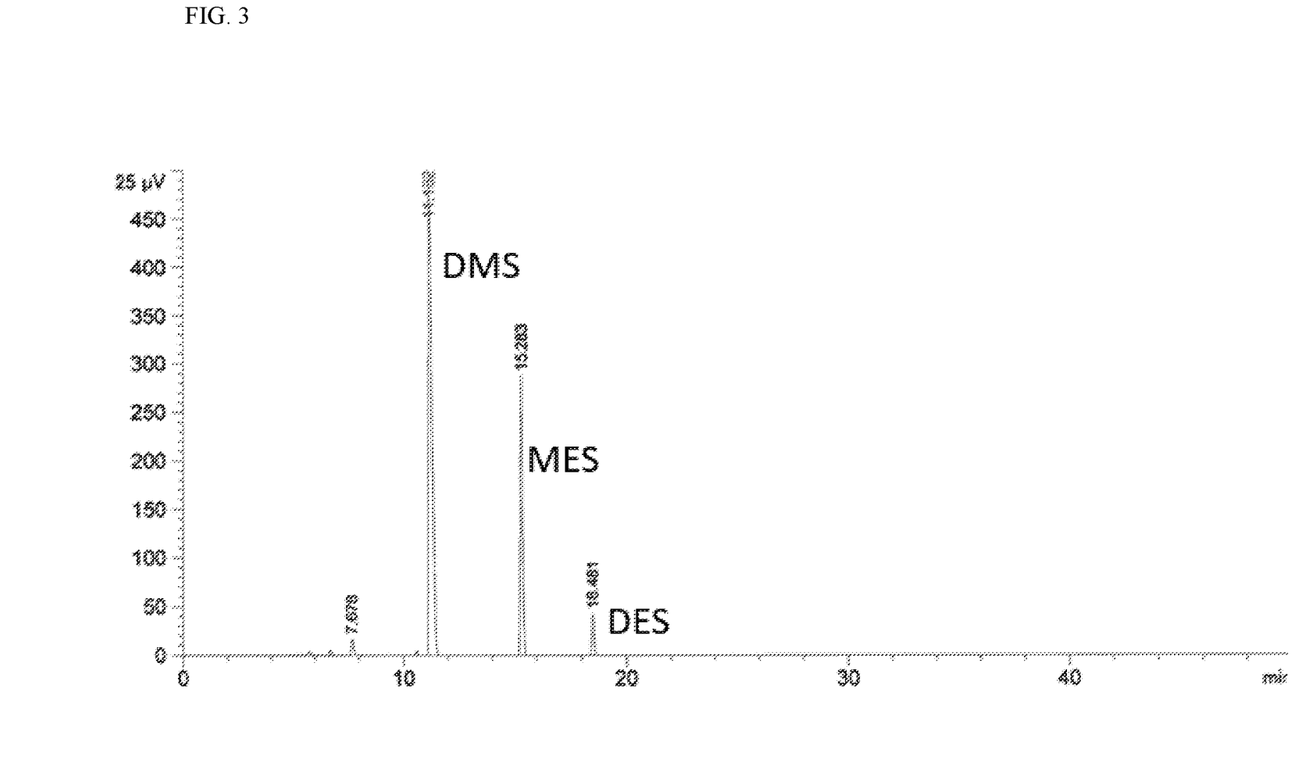
FIG. 3 presents a gas chromatograph plot of the reaction mixture of Example 3 containing methyl ethyl sulfide.

The same general procedure was used for Examples 2-4, and the results are summarized in Table I, with the respective amounts of DMS, DES, and MES in area percentages. The percent conversions of DMS, primarily to MES, were in the 70-80% range. FIG. 3 is a GC plot of the reaction mixture of Example 3, with DMS eluting at 11 min (~67 area %), DES eluting at 18 min (~4.5 area %), and MES eluting at 15 min (~25 area %).

For Examples 5-9, the same general procedure for Example 1 was followed, except that the top zone of the reactor contained 6.92 of inert alumina and 6.90 g of supported CoMo, the middle zone of the reactor contained 3.82 g of inert alumina and 9.47 g of supported CoMo, and the bottom zone of the reactor contained 13.22 g of supported CoMo. The results are summarized in Table I. Generally, the lower reaction temperatures used in Examples 5-9 resulted in significantly lower conversions of DES.

Figure 4:
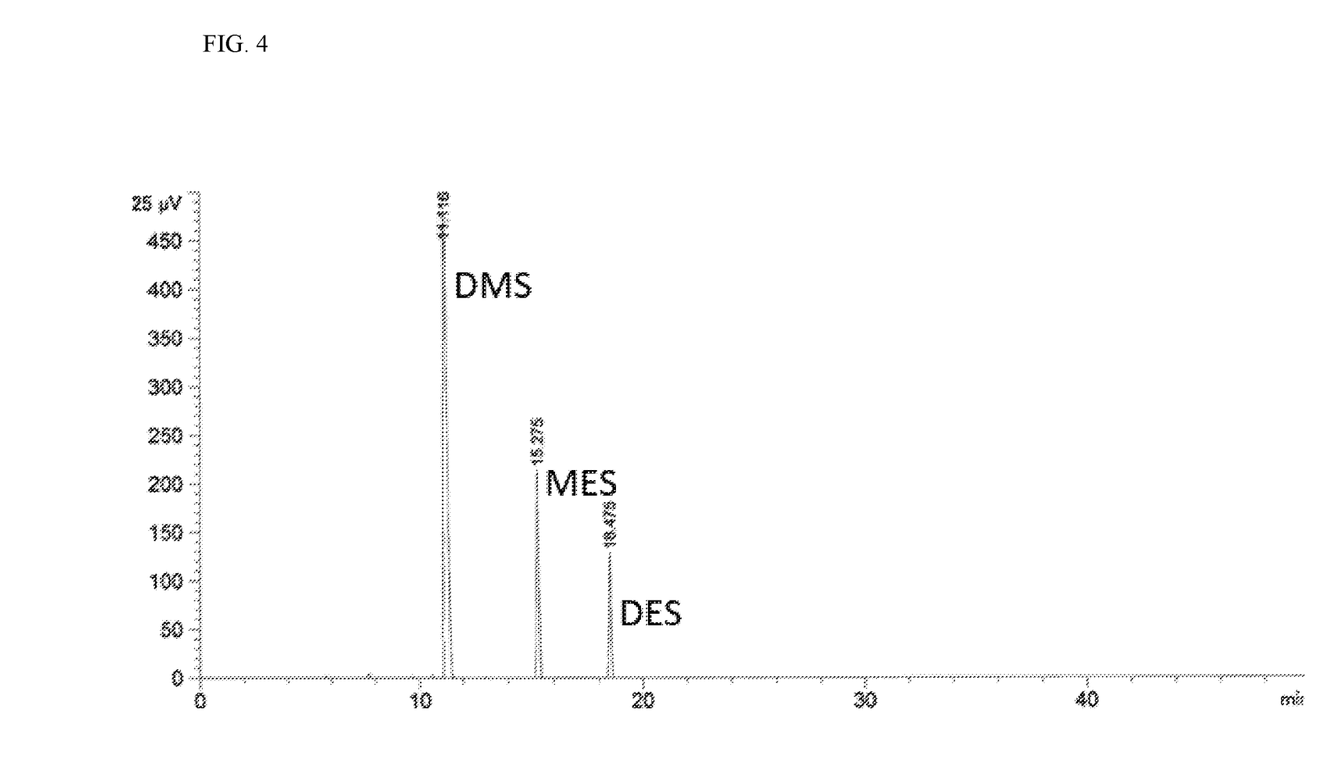
FIG. 4 presents a gas chromatograph plot of a reaction mixture containing methyl ethyl sulfide, produced using a CoMo catalyst.

For Examples 10-13, the same general procedure for Examples 5-9 was followed. The results are summarized in Table I. The reaction temperatures for Examples 11-13 were in the 270-380° C. range and, unexpectedly, 88-91% of the DES was converted, primarily to methyl ethyl sulfide (MES). FIG. 4 is a GC plot of a reaction mixture representative of Examples 5-13, with DMS eluting at 11 min, DES eluting at 18 min, and MES eluting at 15 min.

For Example 14, dimethyl sulfide (DMS) and diethyl sulfide (DES) were blended in a feed tank at an approximate weight ratio of 4:1 (DMS:DES), along with approximately 4.7 wt. % of TBPS 454 di-tert-butyl polysulfide (CAS No. 68937-96-2), based on the total weight of the blended feed. While not wishing to be bound by the following theory, it is believed that the TBPS 454 may decompose to free mercaptan and help initiate the reaction to produce MES. The blended feed was fed into the top of the fixed bed reactor containing only γ-alumina (33.5 g) at a WHSV of 0.2 (weight of DES which comes in contact with the catalyst per unit time, in g/g/hr). The results are summarized in Table I. Unexpectedly, in Example 14, 80% of the DES was converted using only γ-alumina (no CoMo or NiMo), primarily to methyl ethyl sulfide (MES).

Figure 5:
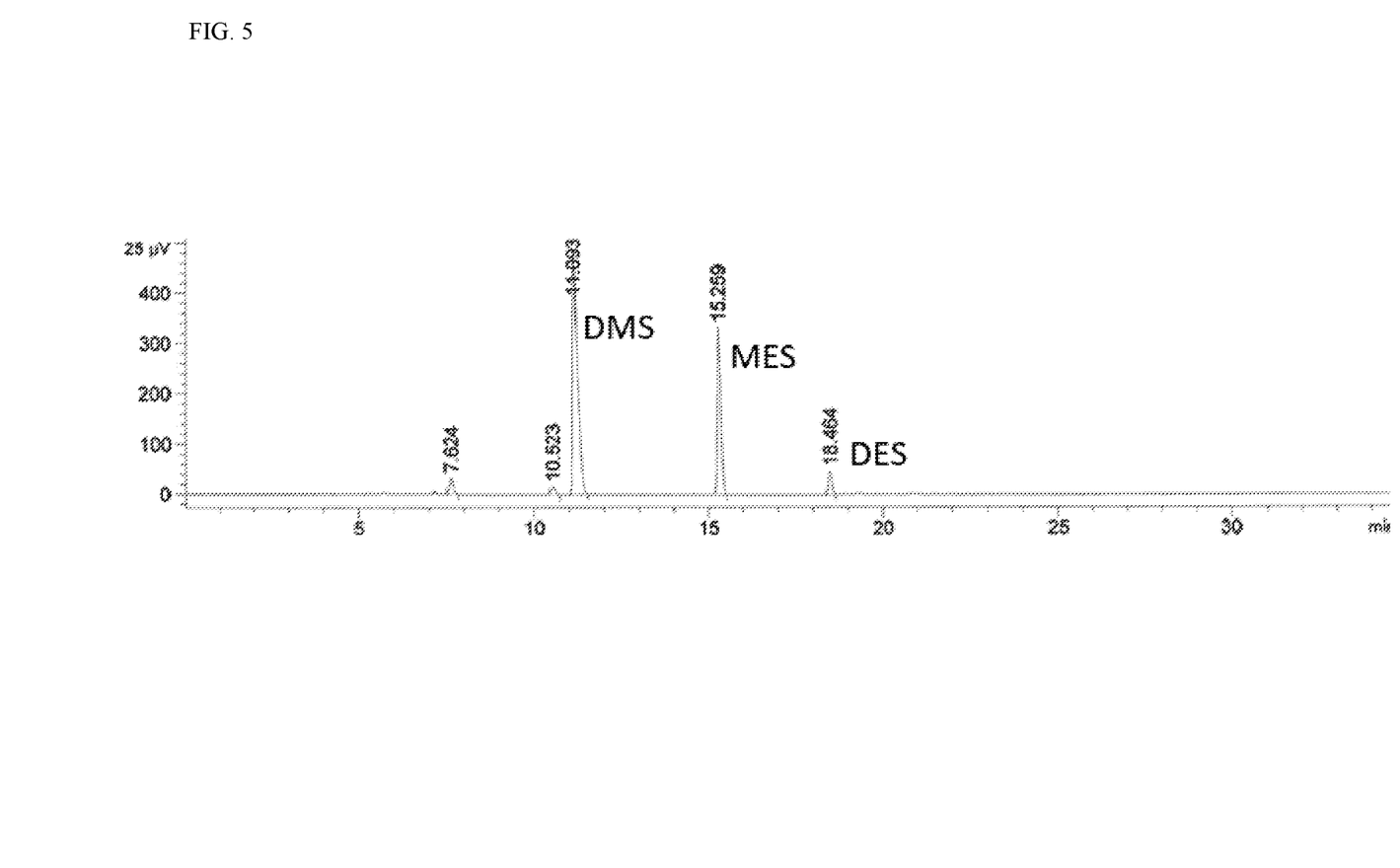
FIG. 5 presents a gas chromatograph plot of a reaction mixture containing methyl ethyl sulfide, produced using a γ-alumina catalyst.

For Example 15, the same general procedure for Example 14 was followed, except that the flow rate was reduced to result in a WHSV of 0.1 (see Table I). Unexpectedly, 87% of the DES was converted using only γ-alumina (no CoMo or NiMo), primarily to methyl ethyl sulfide (MES). FIG. 5 is a GC plot of a reaction mixture representative of Examples 14-15, with DMS eluting at 11 min, DES eluting at 18 min, and MES eluting at 15 min.

Beneficially, and unexpectedly, few by-products were observed in Examples 1-15, and thus purification of the crude MES product would not be problematic. Also surprisingly, only a small amount of methyl mercaptan (MeSH) was present in the reactor effluent; MeSH concentrations were approximately ~0.5-3 wt. % in the reactor effluent, regardless of the catalyst used. Ethyl mercaptan was present at much less than 1 wt. % in the reactor effluent, and often not detectable.

For Example 16, the conditions of Example 14 were utilized, except that the feed ratio of dimethyl sulfide (DMS) and diethyl sulfide (DES) was reversed, such that DMS was the limiting reactant. The molar ratio of DES:DMS was 5:1 in Example 16. Similar to Examples 1-15, MES was produced in Example 16.

TABLE I

Summary of Examples 1-15.

| Example | WHSV | Top (° C.) | Middle (° C.) | Bottom (° C.) | Flowrate (g/hr) | Pressure (psig) | DMS (%) | MES (%) | DES (%) | DES Conversion (%) |
|---|---|---|---|---|---|---|---|---|---|---|
| Feed | — | — | — | — | — | — | 79.30 | 0.00 | 20.70 | — |
| 1 | 0.10 | 269 | 301 | 296 | 17 | 301 | 49.13 | 17.82 | 1.97 | 90.5 |
| 2 | 0.10 | 294 | 309 | 304 | 17 | 295 | 67.87 | 26.50 | 3.93 | 81.0 |
| 3 | 0.10 | 294 | 301 | 298 | 17 | 300 | 67.41 | 25.36 | 4.51 | 78.2 |
| 4 | 0.05 | 292 | 302 | 298 | 9 | 298 | 68.16 | 23.40 | 5.88 | 71.6 |
| 5 | 0.10 | 261 | 149 | 107 | 15 | 313 | 68.65 | 4.87 | 11.66 | 43.7 |
| 6 | 0.10 | 272 | 143 | 99 | 15 | 310 | 68.68 | 16.90 | 8.69 | 58.0 |

TABLE I-continued

Summary of Examples 1-15.

| Example | WHSV | Top (° C.) | Middle (° C.) | Bottom (° C.) | Flowrate (g/hr) | Pressure (psig) | DMS (%) | MES (%) | DES (%) | DES Conversion (%) |
|---|---|---|---|---|---|---|---|---|---|---|
| 7 | 0.42 | 200 | 139 | 29 | 60 | 308 | 67.04 | 20.18 | 12.78 | 38.2 |
| 8 | 0.42 | 291 | 188 | 148 | 60 | 294 | 73.52 | 9.67 | 15.44 | 25.4 |
| 9 | 0.42 | 292 | 190 | 154 | 60 | 294 | 73.45 | 9.82 | 15.37 | 25.7 |
| 10 | 0.10 | 333 | 179 | 122 | 15 | 303 | 72.92 | 15.13 | 10.02 | 51.6 |
| 11 | 0.10 | 340 | 381 | 340 | 15 | 303 | 60.83 | 17.95 | 2.46 | 88.1 |
| 12 | 0.10 | 281 | 286 | 269 | 15 | 298 | 64.24 | 25.84 | 2.12 | 89.7 |
| 13 | 0.10 | 299 | 306 | 297 | 15 | 300 | 65.66 | 25.54 | 2.01 | 90.3 |
| 14 | 0.20 | 297 | 282 | 199 | 33 | 318 | 60.99 | 30.61 | 4.08 | 80.3 |
| 15 | 0.10 | 299 | 281 | 185 | 17 | 308 | 62.49 | 28.57 | 2.74 | 86.8 |

The invention is described above with reference to numerous aspects and specific examples. Many variations will suggest themselves to those skilled in the art in light of the above detailed description. All such obvious variations are within the full intended scope of the appended claims. Other aspects of the invention can include, but are not limited to, the following (aspects are described as "comprising" but, alternatively, can "consist essentially of" or "consist of"):

Aspect 1. A process for producing methyl ethyl sulfide, the process comprising contacting (a) dimethyl sulfide, (b) diethyl sulfide, and (c) a catalyst, to form a reaction mixture comprising the methyl ethyl sulfide.

Aspect 2. The process defined in aspect 1, wherein the dimethyl sulfide and the diethyl sulfide are combined prior to contacting the catalyst.

Aspect 3. The process defined in aspect 1 or 2, wherein the step of contacting is conducted at a temperature in any suitable range or any range disclosed herein, e.g., from about 200° C. to about 500° C., from about 125° C. to about 400° C., or from about 250° C. to about 350° C.

Aspect 4. The process defined in any one of the preceding aspects, wherein the step of contacting is conducted at a pressure in any suitable range or any range disclosed herein, e.g., from about 50 to about 850 psig (344 to 5860 kPag), from about 50 to about 500 psig (344 to 3447 kPag), or from about 150 to about 400 psig (1034 to 2758 kPag).

Aspect 5. The process defined in any one of the preceding aspects, wherein a molar ratio of dimethyl sulfide to diethyl sulfide (DMS:DES) is in any suitable range or any range disclosed herein, e.g., from about 10:1 to about 1:10, from about 5:1 to about 1:5, or from about 2:1 to about 1:2.

Aspect 6. The process defined in any one of the preceding aspects, wherein the diethyl sulfide is a limiting reactant in the production of the methyl ethyl sulfide.

Aspect 7. The process defined in any one of the preceding aspects, wherein a molar ratio of dimethyl sulfide to diethyl sulfide (DMS:DES) is in any suitable range or any range disclosed herein, e.g., from about 1.5:1 to about 10:1, from about 4:1 to about 20:1, or from about 2:1 to about 6:1.

Aspect 8. The process defined in any one of the preceding aspects, wherein the process comprises contacting (a) the dimethyl sulfide and (b) the diethyl sulfide in the vapor phase with (c) the catalyst (e.g., the solid catalyst).

Aspect 9. The process defined in any one of the preceding aspects, wherein the process comprises contacting (a) the dimethyl sulfide and (b) the diethyl sulfide with a fixed bed of (c) the catalyst.

Aspect 10. The process defined in any one of the preceding aspects, wherein the process further comprises contacting (a) the dimethyl sulfide, (b) the diethyl sulfide, (c) the catalyst, and (d) any suitable sulfur-containing compound (e.g., $H_2S$, $CS_2$, di-tert-butyl polysulfide, etc., or any combination thereof) at any suitable amount or an amount in any range disclosed herein, e.g., less than or equal to about 5 mol %, less than or equal to about 3 mol %, or less than about 1 mol %, based on the moles of the limiting reactant.

Aspect 11. The process defined in any one of the preceding aspects, wherein the step of contacting is conducted at any suitable WHSV or a WHSV in any range disclosed herein, e.g., from about 0.01 to about 3, or from about 0.05 to about 1.

Aspect 12. The process defined in any one of the preceding aspects, wherein the catalyst comprises any suitable catalyst or any catalyst disclosed herein, e.g., a solid hydrotreating catalyst such as a CoMo catalyst or a NiMo catalyst, γ-alumina, a zeolite, or any combination thereof.

Aspect 13. The process defined in aspect 13, wherein the catalyst comprises the catalyst supported on any suitable solid oxide or any solid oxide disclosed herein, e.g., silica, alumina, silica-alumina, aluminum phosphate, zinc aluminate, zirconia, thoria, etc., or any combination thereof.

Aspect 14. The process defined in any one of the preceding aspects, wherein a conversion of the limiting reactant (or the yield to the methyl ethyl sulfide) is any percent conversion (or yield) disclosed herein, e.g., at least about 50%, at least about 70%, at least about 80%, at least about 90%, or at least about 95%.

Aspect 15. The process defined in any one of the preceding aspects, wherein a single pass conversion of the limiting reactant (or the single pass yield to the methyl ethyl sulfide) is any single pass percent conversion (or single pass yield) disclosed herein, e.g., at least about 40%, at least about 60%, at least about 70%, at least about 75%, or at least about 80%.

Aspect 16. The process defined in any one of the preceding aspects, further comprising a step of isolating the methyl ethyl sulfide from the reaction mixture using any suitable technique or any technique disclosed herein, e.g., extraction, filtration, evaporation, distillation, or any combination thereof, to form a product stream containing the methyl ethyl sulfide.

Aspect 17. The process defined in aspect 16, wherein isolating comprises a distillation step.

Aspect 18. The process defined in aspect 16 or 17, wherein a yield of the methyl ethyl sulfide in the product stream is at least about 50%, at least about 70%, at least about 80%, at least about 90%, or at least about 95%, based on the limiting reactant.

Aspect 19. The process defined in any one of aspects 16-18, wherein a purity of the methyl ethyl sulfide in the product stream is at least about 80 wt. %, at least about 90 wt. %, at least about 95 wt. %, at least about 97 wt. %, or at least about 99 wt. %, based on the total weight of the product stream.

Aspect 20. An integrated mercaptan and sulfide manufacturing system comprising:

(i) a mercaptan production system capable of producing methyl mercaptan and dimethyl sulfide from methanol and $H_2S$ and capable of producing ethyl mercaptan and diethyl sulfide from ethanol and $H_2S$;

(ii) a DMDS production system for consuming at least a portion of the methyl mercaptan from the mercaptan production system, wherein the DMDS production system is capable of producing dimethyl disulfide from the methyl mercaptan (and, for example, hydrogen peroxide and sodium hydroxide);

(iii) an ETE production system for consuming at least a portion of the ethyl mercaptan from the mercaptan production system, wherein the ETE production system is capable of producing ethylthioethanol from the ethyl mercaptan (and, for example, ethylene oxide); and (iv) a MES production system for consuming at least a portion of the dimethyl sulfide and the diethyl sulfide from the mercaptan production system, wherein the MES production system is capable of producing methyl ethyl sulfide from the dimethyl sulfide and the diethyl sulfide.

Aspect 21. The manufacturing system defined in aspect 20, wherein the MES production system comprises a reactor capable of reacting the dimethyl sulfide and the diethyl sulfide in the presence of a catalyst to form a reaction mixture containing the methyl ethyl sulfide.

Aspect 22. The manufacturing system defined in aspect 20, wherein the MES production system comprises a fixed bed reactor capable of reacting the dimethyl sulfide and the diethyl sulfide in the vapor phase with a fixed bed of a catalyst to form a reaction mixture containing the methyl ethyl sulfide.

Aspect 23. The manufacturing system defined in aspect 21 or 22, wherein the reactor is capable of operating at a temperature in a range from about 200° C. to about 500° C. and at a pressure in a range from about 50 to about 500 psig (344 to 3447 kPag).

Aspect 24. The manufacturing system defined in any one of aspects 21-23, wherein the reactor is constructed of any suitable stainless steel or any stainless steel disclosed herein, e.g., grade 304, 316, 321, 347, 410S, 600, or 800 stainless steel.

Aspect 25. The manufacturing system defined in any one of aspects 21-24, wherein the catalyst comprises a supported or unsupported hydrotreating catalyst, e.g., a CoMo catalyst or a NiMo catalyst.

Aspect 26. The manufacturing system defined in any one of aspects 21-25, wherein the reactor is capable of reacting the diethyl sulfide and an excess of the dimethyl sulfide in the presence of a catalyst to form a reaction mixture containing the methyl ethyl sulfide at any percent conversion of the diethyl sulfide (or yield to the methyl ethyl sulfide) disclosed herein, e.g., at least about 70%, at least about 80%, at least about 90%, or at least about 95%.

Aspect 27. The manufacturing system defined in any one of aspects 21-26, wherein the reactor is capable of reacting the diethyl sulfide and an excess of the dimethyl sulfide in the presence of a catalyst to form a reaction mixture containing the methyl ethyl sulfide at any single pass percent conversion of the diethyl sulfide (or single pass yield to the methyl ethyl sulfide) disclosed herein, e.g., at least about 60%, at least about 70%, at least about 75%, or at least about 80%.

Aspect 28. The manufacturing system defined in any one of aspects 21-27, wherein the MES production system comprises a downstream separations system capable of isolating the methyl ethyl sulfide from the reaction mixture to form a product stream containing the methyl ethyl sulfide.

Aspect 29. The manufacturing system defined in aspect 28, wherein the downstream separations system is further capable of isolating unreacted dimethyl sulfide and diethyl sulfide from the reaction mixture, and recycling the unreacted dimethyl sulfide and diethyl sulfide to the reactor.

Aspect 30. The manufacturing system defined in aspect 28 or 29, wherein the downstream separations system is capable of forming the product stream at a purity of the methyl ethyl sulfide in the product stream of at least about 90 wt. %, at least about 95 wt. %, at least about 97 wt. %, or at least about 99 wt. %, based on the total weight of the product stream.

Aspect 31. The manufacturing system defined in any one of aspects 28-30, wherein the downstream separations system is capable of forming the product stream at a yield of the methyl ethyl sulfide in the product stream of at least about 70%, at least about 80%, at least about 90%, or at least about 95%, based on the diethyl sulfide.

Aspect 32. The manufacturing system defined in any one of aspects 28-31, wherein the downstream separations system comprises at least one distillation column.

Aspect 33. The manufacturing system defined in any one of aspects 20-32, wherein at least about 75 wt. %, at least about 85 wt. %, at least about 95 wt. %, or at least about 99 wt. %, of the methyl mercaptan from the mercaptan production system is consumed in the DMDS production system.

Aspect 34. The manufacturing system defined in any one of aspects 20-33, wherein at least about 75 wt. %, at least about 85 wt. %, at least about 95 wt. %, or at least about 99 wt. %, of the diethyl sulfide from the mercaptan production system is consumed in the MES production system.

Aspect 35. The manufacturing system defined in any one of aspects 20-34, wherein the DMDS production system is capable of converting at least about 80%, at least about 90%, at least about 95%, or at least about 99%, of the methyl mercaptan to the dimethyl disulfide.

Aspect 36. The manufacturing system defined in any one of aspects 20-35, wherein the ETE production system is capable of converting at least about 80%, at least about 90%, at least about 95%, or at least about 99%, of the ethyl mercaptan to the ethylthioethanol.

Aspect 37. An integrated method for producing mercaptans and sulfides, the method comprising: (a) reacting methanol and $H_2S$ to form methyl mercaptan and dimethyl sulfide, (b) reacting ethanol and $H_2S$ to form ethyl mercaptan and diethyl sulfide, (c) reacting at least a portion of the methyl mercaptan with hydrogen peroxide and sodium hydroxide to form dimethyl disulfide, (d) reacting at least a portion of the ethyl mercaptan with ethylene oxide to form ethylthioethanol, and (e) reacting at least a portion of the dimethyl sulfide and the diethyl sulfide to form methyl ethyl sulfide.

Aspect 38. The method defined in aspect 37, wherein the dimethyl sulfide and the diethyl sulfide are reacted in the presence of a catalyst to form a reaction mixture containing the methyl ethyl sulfide.

Aspect 39. The method defined in aspect 38, wherein the catalyst comprises a supported or unsupported hydrotreating catalyst, e.g., a CoMo catalyst or a NiMo catalyst.

Aspect 40. The method defined in any one of aspects 37-39, wherein a percent conversion of the diethyl sulfide (or yield to the methyl ethyl sulfide) is any percent conversion (or yield) disclosed herein, e.g., at least about 70%, at least about 80%, at least about 90%, or at least about 95%.

Aspect 41. The method defined in any one of aspects 38-40, further comprising a step of isolating the methyl ethyl sulfide from the reaction mixture using any suitable technique or any technique disclosed herein, e.g., extraction, filtration, evaporation, distillation, or any combination thereof, to form a product stream containing the methyl ethyl sulfide.

Aspect 42. The method defined in aspect 41, wherein a purity of the methyl ethyl sulfide in the product stream is at least about 90 wt. %, at least about 95 wt. %, at least about 97 wt. %, or at least about 99 wt. %, based on the total weight of the product stream.

Aspect 43. The method defined in any one of aspects 38-42, further comprising a step of isolating unreacted dimethyl sulfide and diethyl sulfide from the reaction mixture, and recycling the unreacted dimethyl sulfide and diethyl sulfide.

Aspect 44. The method defined in any one of aspects 37-43, wherein at least about 75 wt. %, at least about 85 wt. %, at least about 95 wt. %, or at least about 99 wt. %, of the methyl mercaptan produced in step (a) is consumed in step (c).

Aspect 45. The method defined in any one of aspects 37-44, wherein at least about 75 wt. %, at least about 85 wt. %, at least about 95 wt. %, or at least about 99 wt. %, of the diethyl sulfide produced in step (b) is consumed in step (e).

Aspect 46. The method defined in any one of aspects 37-45, wherein at least about 80%, at least about 90%, at least about 95%, or at least about 99%, of the methyl mercaptan is converted to the dimethyl disulfide in step (c).

Aspect 47. The method defined in any one of aspects 37-46, wherein at least about 80%, at least about 90%, at least about 95%, or at least about 99%, of the ethyl mercaptan is converted to the ethylthioethanol in step (d).

We claim:

1. A process for producing methyl ethyl sulfide, the process comprising contacting:
   (a) dimethyl sulfide;
   (b) diethyl sulfide; and
   (c) a catalyst;
to form a reaction mixture comprising the methyl ethyl sulfide.

2. The process of claim 1, wherein the dimethyl sulfide and the diethyl sulfide are combined prior to contacting a fixed bed of the catalyst.

3. The process of claim 1, wherein the step of contacting is conducted at:
   a temperature in a range from about 200° C. to about 500° C.;
   a pressure in a range from about 50 to about 850 psig (344 to 5860 kPag); and
   a WHSV in a range from about 0.01 to about 3.

4. The process of claim 1, wherein a molar ratio of dimethyl sulfide to diethyl sulfide (DMS:DES) is in a range from about 10:1 to about 1:10.

5. The process of claim 1, wherein:
   the diethyl sulfide is a limiting reactant in the production of the methyl ethyl sulfide; and
   a molar ratio of dimethyl sulfide to diethyl sulfide (DMS:DES) is in a range from about 2:1 to about 20:1.

6. The process of claim 1, wherein the process further comprises contacting the dimethyl sulfide, the diethyl sulfide, the catalyst, and a sulfur-containing compound comprising $H_2S$, $CS_2$, di-tert-butyl polysulfide, or any combination thereof.

7. The process of claim 1, wherein the catalyst comprises a hydrotreating catalyst.

8. The process of claim 1, wherein the catalyst comprises a supported CoMo catalyst, a supported NiMo catalyst, γ-alumina, a zeolite, or any combination thereof.

9. The process of claim 1, wherein:
   the reaction mixture contains less than or equal to about 3 wt. % methyl mercaptan and less than or equal to about 1 wt. % ethyl mercaptan;
   a conversion of the diethyl sulfide is at least about 80%; and
   a yield of the methyl ethyl sulfide is at least about 70 mol %, based on the diethyl sulfide.

10. The process of claim 1, further comprising a step of isolating the methyl ethyl sulfide from the reaction mixture to form a product stream containing the methyl ethyl sulfide.

11. The process of claim 10, wherein:
   a yield of the methyl ethyl sulfide in the product stream is at least about 70 mol %, based on the diethyl sulfide; and
   a purity of the methyl ethyl sulfide in the product stream is at least about 90 wt. %, based on the total weight of the product stream.

* * * * *